United States Patent
Yamamoto (10) Patent No.: US 9,670,453 B2
(45) Date of Patent: Jun. 6, 2017

(54) SHEET-SHAPED CELL CULTURE DISSOCIATION SYSTEM AND METHOD

(71) Applicant: Takashi Yamamoto, Kanagawa (JP)

(72) Inventor: Takashi Yamamoto, Kanagawa (JP)

(73) Assignee: TERUMO KABUSHIKI KAISHA (JP)

( * ) Notice: Subject to any disclaimer, the term of this patent is extended or adjusted under 35 U.S.C. 154(b) by 149 days.

(21) Appl. No.: 13/753,290

(22) Filed: Jan. 29, 2013

(65) Prior Publication Data

US 2013/0143315 A1 Jun. 6, 2013

Related U.S. Application Data

(63) Continuation of application No. PCT/JP2011/067435, filed on Jul. 29, 2011.

(30) Foreign Application Priority Data

Jul. 29, 2010 (JP) .................................. 2010-170667

(51) Int. Cl.
| | |
|---|---|
| C12M 1/00 | (2006.01) |
| C12M 3/00 | (2006.01) |
| C12Q 1/06 | (2006.01) |
| G01N 1/28 | (2006.01) |

(52) U.S. Cl.
CPC ............ *C12M 47/04* (2013.01); *C12M 47/02* (2013.01); *C12Q 1/06* (2013.01); *G01N 1/286* (2013.01)

(58) Field of Classification Search
CPC ...... C12M 47/04; C12M 41/36; C12M 41/46; C12M 41/48; C12Q 1/06; C12N 5/00
USPC ......... 435/288.7, 287.2, 289.1, 379; 422/536
See application file for complete search history.

(56) References Cited

U.S. PATENT DOCUMENTS

| 5,162,204 A * | 11/1992 | Matsuzaki et al. ............. 435/29 |
| 5,330,914 A * | 7/1994 | Uhlen et al. .................. 435/270 |
| 5,786,207 A * | 7/1998 | Katz et al. .................... 435/267 |
| 2002/0001577 A1 | 1/2002 | Haverich et al. |
| 2005/0221476 A1 * | 10/2005 | Sen et al. ...................... 435/358 |

(Continued)

FOREIGN PATENT DOCUMENTS

| JP | S61-005796 A | 1/1986 |
| JP | S61-5796 A | 1/1986 |

(Continued)

OTHER PUBLICATIONS

Nakatsugawa et al., JPS61-005796A, English language translation.*
Hiroshi Sakamoto, "JPH05285363A, English language translation".*
International Search Report from the International Bureau of WIPO for International Application No. PCT/JP2011/067435 dated Aug. 23, 2011 and English translation of the same (3 pages).

(Continued)

*Primary Examiner* — Michael Hobbs
*Assistant Examiner* — Liban Hassan
(74) *Attorney, Agent, or Firm* — Fitch Even Tabin & Flannery LLP (57) ABSTRACT

Disclosed is a system for dissociating a sheet-shaped cell culture into individual cells. The system, so configured as to minimize the amount of damage to cells when dissociating a sheet-shaped cell culture into individual cells, in one form includes: (i) a reaction unit that dissociates the sheet-shaped cell culture; (ii) a sensor unit that acquires information relating to a particle size distribution of cells inside the reaction unit; and (iii) an analysis unit that computes the particle size distribution of the cells from the information acquired by the sensor unit and determines and outputs a dissociation state.

6 Claims, 7 Drawing Sheets

(56) References Cited

U.S. PATENT DOCUMENTS

| | | | |
|---|---|---|---|
| 2007/0092492 A1 | 4/2007 | Matsuda et al. | |
| 2008/0166037 A1* | 7/2008 | Mandrachia et al. | 382/133 |
| 2009/0221075 A1 | 9/2009 | Dorian et al. | |
| 2009/0222218 A1* | 9/2009 | Chamberlin | G01J 3/10 |
| | | | 702/23 |
| 2009/0242799 A1* | 10/2009 | Bolotin | G01N 15/1459 |
| | | | 250/459.1 |

FOREIGN PATENT DOCUMENTS

| | | |
|---|---|---|
| JP | 2006-238707 A | 9/2006 |
| JP | 2007-089442 A | 4/2007 |
| JP | 2007-528755 A | 10/2007 |
| JP | 2010-029680 A | 2/2010 |
| JP | 2010-081829 A | 4/2010 |

OTHER PUBLICATIONS

Written Opinion of the International Searching Authority and International Search Report from the International Bureau of WIPO for International Application No. PCT/JP2011/067435, dated Aug. 23, 2011 (6 pages) and English translation of the same (4 pages).

Extended European Search Report and European Search Opinion issued in counterpart European Application No. 11 812 619.2, dated Dec. 3, 2013 (5 pages).

European Office Action dated Jan. 28, 2015 for European Patent Application No. 11 812 619.2.

European Office Action dated Jul. 14, 2015 for European Patent Application No. 11 812 619.2.

* cited by examiner

SHEET-SHAPED CELL CULTURE DISSOCIATION SYSTEM AND METHOD

CROSS-REFERENCE TO RELATED APPLICATIONS

This application is a continuation of International Application Number PCT/JP2011/067435, filed on Jul. 29, 2011, which claims priority from JP 2010-170667, filed on Jul. 29, 2010, which are hereby incorporated herein by reference in their entirety.

FIELD OF THE INVENTION

The present invention relates to a system and method for dissociation of a sheet-shaped cell culture and also to a system and method for evaluation of the state of dissociation of a sheet-shaped cell culture.

BACKGROUND OF THE INVENTION

Despite recent innovative progress in the therapy of heart diseases, no firm therapeutic system has been established yet for severe heart failure. A common method for treating heart failure is that of medical therapy by means of β blockers or an ACE inhibitor. Heart failure too severe to be effectively cured by such therapy is treated by replacement therapy with an auxiliary artificial heart or by heart transplantation, i.e., surgical therapy.

There are various causes for severe heart failure such that surgical therapy is needed. They include proceeded valvular disease, hyper myocardial ischemia, acute myocardial infarction and its complications, acute myocarditis, chronic cardiac failure due to ischemic cardiomyopathy (ICM), dilated cardiomyopathy (DCM) or the like, and its acute exacerbation.

Various techniques are applied to the foregoing diseases depending on their cause and severity. They include valvuloplasty, replacement, coronary artery bypass, left ventricular plasty, and mechanically assisted circulation.

It has been thought that the only way for effective treatment of cardiac failure resulting from the severely decreased function of left ventricle due to ICM or DCM is replacement therapy involving heart transplantation or an artificial heart. However, replacement therapy for severe cardiac failure patients has many problems including a constant insufficient number of donors, the necessity for continuous immunosuppression, and various other complications. Therefore, it would be difficult to say that replacement therapy is universally acceptable for treating severe cardiac failure.

In order to cope with the harsh situation surrounding heart transplantation, attempts were made for a period of time to apply other surgical therapies such as the Batista operation procedure. This procedure attracted great attention as a substitute for heart transplantation. However, its limitations recently have been identified, and efforts are being made to improve this surgical procedure and its adequate application.

Under these circumstances, regenerative medicine is being developed as a new means for treating severe heart failure.

Severe myocardial infarction or the like leads to incompetence of myocardial cells, which can further progress to the proliferation of fibroblasts and fibrosis of stroma, and eventually to heart failure. The progress of heart failure damages and kills myocardial cells. As a result, myocardial cells, hardly undergo minimum cell division, decrease in number, thereby rendering the cardiac function even more incompetent.

It is considered that an effective way to reestablish healthy cardiac function for patients that have experienced severe heart failure is by cell transplantation. In fact, the transplantation of autoskeletal myoblasts has already reached the stage of clinical application.

Recently, for this purpose, a three-dimensional sheet-shaped cell culture, for treating the heart and containing cells derived from any part of an adult other than cardiac muscle, and a method for production thereof have been realized by tissue engineering that employs temperature-responsive culture dishes (Japanese Patent Laid-Open No. 2007-528755).

Quality control is needed for putting the above-mentioned cell culture to clinical use via a quality test to establish the effectiveness and safety thereof. A quality test for a sheet-shaped cell culture involves the counting of cells constituting the cell culture and an evaluation of the cells' viability and purity. An essential procedure for such evaluation is the dissociation of the cell culture into individual cells by enzymatic digestion or the like. At present, the dissociation of a cell culture, is for example, accomplished manually by placing a batch of the cell culture in a tube, adding an enzyme such as trypsin to the tube, accelerating the enzymatic reaction in an incubator, thereby breaking the bonds between cells, stirring the tube removed from the incubator after incubation for a prescribed period of time, and observing the contents in the tube to ensure the dissociation of cultured cells. If the dissociation is not completed, the tube is put back in the incubator and then the foregoing procedure is repeated until the dissociation is completed.

The dissociation of cell cultures by enzymatic reactions should be carried out completely, with no aggregated cells remaining, so that dissociated cells can be adequately examined. On the other hand, prolonged enzymatic reactions damage cells, thereby preventing adequate cell examination. Therefore, the enzymatic reaction for cell dissociation should be carried out in as short a time as possible. This necessitates frequent observations of cells during enzymatic reactions for determining whether suitable dissociation has occurred. Nevertheless, there has been no mechanized or automated process for determining the state of cell dissociation. In fact, visual observation by an operator has been required. This procedure makes it difficult to optimize the duration of enzymatic reactions and is very labor intensive for the operator.

SUMMARY OF THE INVENTION

The present invention is concerned with an adequate procedure for dissociation of a cell culture by enzymatic digestion or the like, the procedure being intended for quality control of sheet-shaped cell cultures to be used to cure human and animal diseases and wounds. In order to properly confirm characteristics of dissociated cells, it is desirable to carry out cell dissociation by as few steps as possible without damage to cells, and it is also desirable to prepare completely dissociated cells free of cell aggregates. Thus, it is an object of the present invention to provide a system by which a dissociation process of cells constituting a sheet-shaped cell culture, for preparing suitable cells for quality control of the cell culture, can be carried out in a simple and assured way.

The present inventor carried out research concerning dissociation of a sheet-shaped cell culture to obtain cells suitable for quality control of the cell culture. As a result of the research, it was determined that in order to obtain the desired cells, the dissociation should be conducted under adequate temperature conditions for an enzymatic reaction in the presence of trypsin or the like, added as a cell dissociating agent, with adequate stirring and frequent observation. Besides, excessive enzyme treatment and stirring would damage the cells and raise the risk of contamination. In order to minimize the steps for dissociation, therefore, the present inventor continued the research, and determined that it is possible to mechanically evaluate the state of dissociation of a sheet-shaped cell culture on the basis of a particle size distribution of dissociated cells and that it is possible in this way to automatize the entire process for cell dissociation. Based on these findings, the present system and method have been developed.

Thus, the present invention relates to the following.

(1) A system for dissociating a sheet-shaped cell culture into individual cells, including:

(i) a reaction unit which dissociates the sheet-shaped cell culture;

(ii) a sensor unit which acquires information about a particle size distribution of cells existing in the reaction unit; and (iii) an analysis unit which calculates the particle size distribution of cells from the information acquired by the sensor unit, thereby determining and outputting a state of dissociation.

(2) The system as defined in the above paragraph (1), wherein the sheet-shaped cell culture contains a skeletal myoblast.

(3) The system as defined in the above paragraph (1) or (2), further including a reaction control unit which controls the dissociation of cells in the reaction unit.

(4) The system as defined in the above paragraph (3), wherein the reaction control unit includes at least one of an environment control unit, a chemical action control unit, and a mechanical action control unit.

(5) A system for determining a state of dissociation of a sheet-shaped cell culture in a treatment for dissociating the sheet-shaped cell culture into individual cells, including:

(i) a sensor unit which acquires information about a particle size distribution of cells in the sheet-shaped cell culture having undergone a dissociation treatment; and (ii) an analysis unit which calculates the particle size distribution of cells from the information acquired by the sensor unit, thereby determining and outputting the state of dissociation.

(6) A method of dissociating a sheet-shaped cell culture into individual cells, the method including the steps of:

(i) subjecting the sheet-shaped cell culture to a dissociation treatment;

(ii) acquiring information about a particle size distribution of cells in the sheet-shaped cell culture having undergone the dissociation treatment; and (iii) calculating the particle size distribution of cells from the acquired information, thereby determining and outputting a state of dissociation.

(7) A method for determining a state of dissociation of a sheet-shaped cell culture, the method including a step of determining and outputting the state of dissociation based on a particle size distribution of cells in the sheet-shaped cell culture having undergone a dissociation treatment.

(8) The method as defined in the above paragraph (6) or (7), wherein the sheet-shaped cell culture contains a skeletal myoblast.

The system according to the present invention is intended to prepare cells suitable for quality control of a sheet-shaped cell culture. To this end, the system performs the dissociation of cells constituting a sheet-shaped cell culture automatically in a simple and reliable way, with minimal damage to cells being dissociated and maximizing labor-savings for the operator. With an incubator for cell cultivation, an apparatus for peeling off a sheet-shaped cell culture, and an apparatus for analyzing the characteristic properties of dissociated cells (for example an apparatus for counting the number of cells (such as Coulter counter, made by Beckman Coulter, Inc.), an apparatus for automatically measuring viability of cells, and a flow cytometer for measuring the purity of cells) integrally provided, it is possible to automatize all the steps from cell cultivation and preparation of a sheet-shaped cell culture to the quality control of the sheet-shaped cell culture.

DETAILED DESCRIPTION OF THE PREFERRED EMBODIMENTS

The present invention is concerned with a system for dissociating a sheet-shaped cell culture into individual cells, including:

(i) a reaction unit which dissociates the sheet-shaped cell culture;

(ii) a sensor unit which acquires information about a particle size distribution of cells existing in the reaction unit; and (iii) an analysis unit which calculates the particle size distribution of cells from the information acquired by the sensor unit, thereby determining and outputting a state of dissociation.

The present system may optionally include a reaction control unit which controls the dissociation of cells in the reaction unit.

The "sheet-shaped cell culture" which undergoes dissociation in the system according to the present invention contains any cells capable of forming cell cultures in sheet form. Examples of such cells are not restricted and include myoblasts (such as skeletal myoblasts), myocardial cells, fibroblasts, synovial cells, epithelial cells, and endothelial cells. Preferable among these are those capable of forming cell cultures in monolayer shape, e.g., myoblasts, in the present invention. Any cells are acceptable which are derived from living beings that can be cured with cell cultures. Examples of such living beings are not restricted and include human being, primates other than human, dogs, cats, pigs, horses, goats, and sheep. One or more than one kind of cells may be used to form the sheet-shaped cell culture. According to a preferred embodiment of the present invention, the majority of cells in the sheet-shaped cell culture formed from more than one kind of cells account for 65% or more, preferably 70% or more, and more preferably 75% or more, of the total cells in the cell culture, when the production of the cell culture is completed. This percentage represents purity.

The term "sheet-shaped cell culture" as used in the present invention denotes an object in sheet form composed of cells joined together. This object is typified by cells arranged in a single layer, or double or multiple layers. Cells may be joined together directly and/or indirectly (with an intermediate among them). Such an intermediate is not specifically restricted so long as it is capable of joining cells together at least physically (mechanically). One of its examples is an extracellular matrix. The intermediate is preferably one that is derived from cells, particularly one derived from cells constituting the cell culture. The physical (mechanical) joining may be combined with functional (chemical or electrical) joining.

The sheet-shaped cell culture that is to be subject to the dissociation treatment of the present invention may be in contact with or separated from a culture medium such as a culture container. In the former case, the sheet-shaped cell culture may be transferred, together with the culture medium, from a cultivation unit into the system of the present invention. Alternatively, it is possible to carry out separation from the culture medium and dissociation of cultivated cells at the same time. In the latter case, the container holding the sheet-shaped cell culture separated from the culture medium may be used as a reaction vessel of the present system. Alternatively, it is also possible to separate the sheet-shaped cell culture and to transfer it from the container to the reaction vessel of the system. The sheet-shaped cell culture in the present invention may be a representative one of a sheet-shaped cell culture lot composed of a plurality of sheet-shaped cell cultures produced under the same conditions.

The sheet-shaped cell culture according to the present invention preferably includes no scaffold (support). A scaffold is an item which is sometimes used in the field of this technology so that it supports cells thereon and/or therein, thereby keeping the cell culture physically integral. It may be typified by a scaffold made of synthetic polymer such as polyvinylidene difluoride (PVDF), polylactic acid (PLA), and polyglycolic acid (PGA). However, such a scaffold is not necessary for the cell culture used in the present invention to remain physically integral. The cell culture used in the present invention is preferably composed only of a material derived from the cells constituting the cell culture and free of any other material. In a case where a scaffold is included in the sheet-shaped cell culture, it may be removed by an additional step that precedes the step of acquiring information about the particle size distribution.

The term "reaction unit" used herein denotes that part of the system which performs the dissociation of a sheet-shaped cell culture and from which the information about particle size distribution is acquired. The reaction unit includes the reaction vessel (which holds therein the sheet-shaped cell culture) and a support unit (which supports the reaction vessel). The reaction vessel and the support unit may be separated from or integral with each other.

The reaction vessel is not specifically restricted so long as it enables the operations of accommodating the sheet-shaped cell culture, performing dissociation, and acquiring the information about particle size distribution. It may be a commercial cell container, such as a Petri dish, tube, and flask, or a custom-made one. It may widely vary in material, shape, and dimensions. The dissociation of a sheet-shaped cell culture is performed in a medium suitable for the life of cells such as medium, physiological saline or PBS by the action of a cell dissociating agent or the like. Therefore, the reaction vessel is preferably made of any material that is impermeable to such liquid, that is inert and resistant to the cell dissociating agent or the like, and/or that does not affect the state of the cells. In addition, the reaction vessel may be in the shape of polyhedron, cone, sphere, hemisphere, or a combination thereof, which have one or more than one surface, side, and/or apex. A shape having at least one flat surface for cell observation may be adopted. The reaction vessel is not specifically restricted in dimensions. Adequate dimensions can be determined according to the size of the sheet-shaped cell culture and the method for acquiring information about particle size distribution. For example, a preferable maximum sectional area may range from 1 to 400 $cm^2$, 4 to 225 $cm^2$, 9 to 144 $cm^2$, 16 to 100 $cm^2$, or 25 to 81 $cm^2$, and a preferable maximum diameter of the sectional area may range from 1 to 20 cm, 2 to 15 cm, 3 to 12 cm, 4 to 10 cm, or 5 to 9 cm. The reaction vessel may be either a repeatedly usable one or a disposable one. Moreover, the reaction vessel may have at least one opening on the top or any other part thereof, and the opening may optionally be closed with a lid or the like to avoid contamination or for other purposes.

The support unit is not specifically restricted so long as it is capable of at least stably supporting the reaction vessel. It may be custom-made or converted from a commercial incubator, thermostat, heat block, hot plate, or shaker.

The reaction unit (reaction vessel and/or support unit) may be made entirely or partly of any light transmitting material. In a case where the reaction vessel is at least made of a light transmitting material, particularly of a transparent material, optical information (such as image and laser diffraction pattern) about the dissociation state of a sheet-shaped cell culture in the reaction vessel is permitted to be acquired from the outside of the reaction vessel while the reaction vessel is closed. In this case, as long as part of the vessel necessary for acquiring the optical information is made of a light transmitting material, a similar advantage can be obtained even if a part of the vessel other than the part necessary for acquiring the optical information is made of a light blocking material. The reaction vessel may also be covered with a light blocking material for protection from the effect of external light.

The reaction unit may be a ready-made one or a custom-made one suitable for an applicable method for the determination of particle size distribution. The reaction vessel may be at least partly transparent or may be opened, for example in a case where an image analysis method or a laser diffraction scattering method using the optical information is used for the determination of particle size distribution. The reaction vessel may also have a flat bottom for uniform observation of cells. The bottom of the reaction vessel may have a surface area which is equal to or larger than the area of the sheet-shaped cell culture to be dissociated so that cells do not planarly overlap with one another during the process of image acquisition or laser illumination. For example, the ratio between the two areas may be 1.1 times or more, 1.25 times or more, 1.5 times or more, or two times or more. In addition, a sampling port for guiding cells to the sensor unit during the dissociation treatment may be provided. The sampling port may be, for example, a plastic or metal tube through which cells under the dissociation treatment can be sucked out. In a case where a light source is used for the acquisition of optical information, the reaction unit (or the support unit) may be provided with a light source (such as a lamp), an optical fiber connected to the lamp, a laser, and means for reflecting light (such as a reflector), or the like. The light source may be attached for example to the support unit close to the light transmitting part of the reaction vessel. The position of the light source is not specifically restricted so long as the sensor unit can successfully acquire images. The light source may be disposed at one location of the top, bottom and lateral faces of the reaction vessel. Alternatively, a plurality of light sources may be arranged at plural locations of the top, bottom, and lateral faces of the reaction vessel. A plurality of reaction vessels may be arranged on one support unit so that a series of information can be acquired simultaneously or sequentially from the plural reaction vessels.

In a case where an electrical sensing zone method is employed, the reaction vessel may be constructed, for example, such that it is divided into at least two compartments connected through a small hole (aperture). This aperture permits cells being dissociated to pass therethrough, and data (in terms of change in a voltage pulse or the like) can be acquired during the passage of cells. Specifically, for example, the heights of the two compartments may be adjusted by the support unit so that cells in the reaction vessel pass through the aperture by their own weight or together with water flow induced by gravity. In this case, the two compartments divided by the aperture may be arranged such that one is positioned higher than the other and vice versa, so that cells move in both directions through the aperture. Data acquisition may be possible while cells are moving in either direction or both directions. In the former case, the two compartments may be connected through an additional passage which is opened only when the process of data acquisition is idle. According to another embodiment, the reaction vessel may have a roughly toroidal shape. This reaction vessel has an aperture for cell passage at least one position. Cells are caused to pass through this aperture together with water flow which circulates in the reaction vessel and passes through the aperture. In any of the foregoing embodiments, the aperture may be formed to be tapered (mortar-shaped) upstream in order to prevent cells from sticking to the surrounding of the aperture and from being damaged during passage. Here, "upstream" is determined based on the direction of the flow of cells. For cells flowing in one direction only, the aperture may have a corresponding side thereof formed to be tapered. For those cells flowing in both directions, the aperture may have both sides thereof formed to be tapered. The above-mentioned structure ensures that promotion of the dissociation of cells by liquid flow and acquisition of information about particle size distribution can be performed concurrently.

The "sensor unit" in the system according to the present invention is intended to acquire information about the particle size distribution of cells existing in the reaction vessel. Information about particle size distribution includes, for example, images (both still and video), changing electrical signals, laser diffraction pattern, and three-dimension measurements. Any information type may be acquired as long as it is suitable for the calculation method of specific particle size distribution to be used. The particle size distribution may be calculated by any one of several known methods including the image analysis method, laser diffraction scattering method, and electrical sensing zone method. These methods may be used in combination with one another.

The image analysis method is designed to analyze an acquired image and measure the size and number of particles (or cells) contained in the image, thereby calculating the particle size distribution. Specifically, this method consists of the steps of analyzing images acquired from an image acquisition or capturing device for example from a CCD camera alone or combined with a microscope, extracting contours of individual cells or cell aggregates from the images, calculating parameters relating to particle size, and determining the particle size distribution from the thus calculated data. The parameters relating to particle size include breadth, length, distance between two parallel tangents (Feret diameter), maximum diameter in a given direction (Krummbein diameter), length of a line that divides the area into two equal areas (Martin diameter), long-short mean diameter, circumscribed rectangular equivalent diameter, square equivalent diameter, circle equivalent diameter (Heywood diameter), and projected area. Those images used to extract the contour of individual cells or cell aggregates are images with enhanced contours such as a dark-field image, a phase contrast image and a differential interference image. Only way of enhancing the contour of cells is by staining cells with a dye that stains cytoplasm and the cell membrane. The image analysis method merely needs means for acquiring an image in the reaction vessel such as a CCD camera. This makes the apparatus simple in structure and provides more freedom in the design of the apparatus.

Images may be acquired from the entire contents of the reaction vessel or from a portion of the contents of the reaction vessel. In the latter case, images may be obtained from one position in the reaction vessel, or from plural positions (two, three, four, five, six, seven, eight, nine, ten or more positions) in the reaction vessel. Samples may also be obtained through the sampling port from one or more than one position in the reaction vessel.

The laser diffraction scattering method is intended to calculate the particle size distribution on the basis of laser diffraction/scattering patterns that appear when particles (cells, for example) in a medium are illuminated with a laser beam via a laser and detector device, as described further herein. A laser beam directed to particles gives rises to diffraction/scattering patterns characteristic of particle size. This phenomenon is used to estimate the particle size. For example, those particles which are larger relative to the laser beam cause the diffraction/scattering light to converge forward (in a direction in which the laser beam advances). As the particles become smaller, the diffraction/scattering light is broadly distributed in a lateral direction. In a case of much smaller particles, the distribution also expands rearward. This makes it possible to estimate the size of individual particles by detecting the distribution of diffraction/scattering light (for example, the distribution of light intensity). This method, which is designed to detect the distribution of diffraction/scattering light, permits the particle size distribution to be calculated in a short time because of the comparatively simple data processing involved and the short measuring time required. Therefore, it is possible to easily perform the calculation of particle size distribution frequently and in real time. In addition, it is possible, for example, to modify the method so as to detect only those particles which are not less than or not more than a prescribed size if a detection unit is properly adjusted for detection position and detection sensitivity. This makes it possible to efficiently acquire only necessary data without acquiring data of all the particles, thereby improving processing efficiency.

The diffraction/scattering patterns may be acquired from the entire contents of the reaction vessel or from a portion of the contents of the reaction vessel. In the latter case, patterns may be obtained from one position in the reaction vessel, or from plural positions (two, three, four, five, six, seven, eight, nine, ten or more positions) in the reaction vessel. Samples may also be obtained through the sampling port from one or more than one position in the reaction vessel.

The electrical sensing zone method is designed to estimate the volume of individual particles based on the fact that an electrolytic solution containing particles changes in electric resistance (impedance) in a small aperture when particles pass through the small aperture. When particles pass through the small aperture, the electrolytic solution in the small aperture is replaced with the particles by the volume of the particles. The impedance of the electrolytic solution in the small aperture changes in proportion to the volume of the replaced electrolytic solution. The impedance that changes in this manner can be measured, for example by applying an electric current across the small aperture and detecting changes in the voltage pulse by an electrical resistance measururing device, as described further herein. This method, which utilizes results of electric measurements, permits data processing in a comparatively simple manner. Moreover, it may be used even under conditions that involve difficulties in extraction of the contour of cells or cell aggregates.

The sensor unit may include any additional means of acquiring information necessary for the calculations mentioned above. For example, the additional means useful for the image analysis method may include a lens (to optically enlarge or reduce images), a CCD camera, a light source, a reflector, and an amplifier (such as an optical signal amplifier and an electrical signal amplifier). Also, the additional means useful for the electrical sensing zone method may include an electric or electronic circuit, a small hole (aperture) for a cell to pass through, an element for measurement of electrical resistance or voltage pulses, and a digital waveform analyzing and processing circuit. In the case of the laser diffraction/scattering method, the additional means may include a laser, a Fourier lens, a multidetector, and a CMOS sensor.

The sensor unit may further acquire information about the environment in the reaction vessel. Information such as the temperature, humidity, pressure, illuminance, concentration of carbon dioxide, concentration of enzyme, and vibration in the reaction unit may be measured.

Incidentally, such information (including information about the particle size distribution and information about the environment inside the reaction unit) may be one which is acquired at a specific time point, at plural time points in regular intervals, or in real time.

The sensor unit may be independent from or integral with the reaction unit. For example, the sensor unit may be installed on the support unit which is arranged on the upper side, lateral side, and/or lower side of the reaction vessel. In a case where the reaction unit has more than one reaction vessel or the system of the present invention has more than one reaction unit, there may be as many sensor units as reaction vessels or reaction units or there may be only one sensor unit which takes care of more than one reactor vessel or reaction unit. In this case, an arrangement may be made such that the sensor unit is stationary and the reaction vessels and reaction units are movable to positions for measurement by the corresponding sensor unit or such that the reaction vessels and reaction units are stationary and the sensor unit is movable to a position of measurement corresponding to each of the reaction vessels and the reaction units. In the former case, the support unit is, for example, rotatably installed and the plural reaction vessels are installed in a circular arrangement on the support unit, so that the reaction vessels may be moved sequentially to positions for measurement as the support unit rotates.

The "analysis unit" in the present invention receives information from the sensor unit and analyzes the received information. The analysis unit includes at least a processor which receives information from the sensor unit and analyzes the received information. It may also additionally include a storage unit, a control unit, an input unit, and an output unit. The storage unit stores information received from the sensor unit and also stores the results of analysis. The storage unit includes a variety of electronic recording media such as semiconductor memory and a hard disc. The control unit sends out a signal to the reaction control unit or the like according to the results of analysis and includes a signal generation circuit etc. The input unit permits a system user or another system to input information (such as a preset parameter) according to need. The input unit includes a variety of input interfaces, for example means of receiving electrical and optical signals from another system (such as wire, optical fiber, connector and wireless communication device), button, keyboard, touch panel, and so on. The output unit sends out a predetermined signal based on the results of analysis. The output unit includes a variety of output interfaces, for example means of transmitting electrical and optical signals to another system or the like (such as wire, optical fiber, connector and wireless communication device), monitor, printer, indicator lamp, buzzer, voice synthesizer, and so on. The input unit and the output unit may be integrated into a single input-output interface including an input interface and an output interface. This may be realized by using a general-purpose computer.

The analysis unit carries out following processing, for example. First, the analysis unit receives information from the sensor unit. Then, it calculates the particle size distribution of cells and the environment in the reaction unit, which are measured parameters. The analysis unit compares the measured parameter with a preset parameter. The analysis unit determines from the results of comparison the degree of dissociation of cells and the state inside the reaction unit and determines whether or not the dissociation is completed or whether or not to stop the dissociation step. The preset parameter necessary for analyzing the state of dissociation may be one which has been previously established or which has been entered by the system user with the input unit. If it is determined that the dissociation is completed, the control unit may be caused to send out a signal to stop the dissociation step. If it is determined that the dissociation is not yet completed, the control unit may be caused to send out a signal to continue the dissociation step.

A signal to stop the dissociation step may be sent out even if dissociation is still incomplete, for example after lapse of a prescribed period of time or after dissociation to a prescribed extent. The prescribed period of time may be 0.5 to 30 minutes, 1 to 25 minutes, 2 to 20 minutes, 3 to 15 minutes, 4 to 12 minutes, or 5 to 10 minutes, without specific restrictions. Dissociation to a prescribed extent may mean that dissociation has proceeded to such an extent that single cells account for not less than 50%, 60%, 70%, 80%, 90%, or 95% in number or volume of the total cells. Even if there exist some cell aggregates, it is possible to remove them by using a cell strainer (or any other separating means) and take out only single cells that can be used for various measurements necessary for a quality control process that follows.

The above-mentioned signals are sent to the reaction control unit which controls the dissociation process. Also, the control unit can control the sensor unit as well as the position and time for measurement in the reaction unit. Therefore, the above-mentioned preset parameter may be one which includes a pattern that changes with time. The output unit may display on the monitor the preset parameter, the measured parameter, an image obtained from the sensor unit and the like. Alternatively, it may turn on the indicator lamp that indicates the completion of dissociation. The completion of dissociation may be announced to the user by means of the buzzer or sound output such as audio assist, or transmitted to another system by means of an electrical signal or an optical signal.

The calculated particle size distribution may be compared with the preset parameter in any one of following ways. Comparison may be made between an average particle diameter (calculated from the information about particle size distribution obtained previously) and the previously established corresponding average particle diameter. In this case, the average particle diameter to be calculated is not restricted and may be any one of a number mean diameter, length mean diameter, area mean diameter, mass mean diameter, mean surface area diameter, mean volume diameter, equivalent specific surface diameter, median diameter, modal diameter and the like. Comparison may also be made between the number or volume of particles having diameters not smaller than or not larger than the preset diameter (or the ratio of such particles to the total) and the previously established values. Comparison may further be made between a shape of a diagram of particle size distribution and a shape of previously diagram of particle size distribution one. In a case where the dissociation of cells does not proceed sufficiently, the resulting average particle diameter is usually larger compared with one in a case where the dissociation is completed (that is, there exist no cell aggregates at all) or a case where the dissociation proceeds to a sufficient extent because incomplete dissociation leaves a large amount of cell aggregates consisting of plural cells joined together. This applies also to the number or volume of, or the ratio to the total of the number or volume of, particles not smaller than the preset particle diameter. In addition, the resulting diagram of particle size distribution has not only a peak centered at an average particle diameter of single cells but also one or plural peaks at larger average particle diameters (usually in the right side in the diagram). According as the dissociation treatment proceeds, cell aggregates separate into individual cells and the measured parameter mentioned above changes. A setting may be made such that it is determined that the dissociation is completed when the measured parameter mentioned above agrees with the previously established parameter.

The information supplied from the analysis unit permits the system itself and/or the system user to alter the preset parameter, to take out dissociated cells and send them to a next step, or to perform an ensuing treatment on the dissociated cells. Preset parameters may include, in addition to parameters relating to the particle size distribution of cells, characteristics of dissociation reaction, temperature adequate to dissociation, concentration of enzyme, duration of treatment, and amplitude and period of oscillation. The input unit may function also as a control switch, so that it is possible to operate the camera, light source and the like through the sensor unit, thereby obtaining the state of cell dissociation, and to manually enter optimal parameters through the input unit to alter the preset parameters. The storage unit stores the series of processes for altering the preset parameters mentioned above, the measured parameters, and the results of analysis. Therefore, it is possible to obtain the change in the particle size distribution that occurs during the dissociation of various cell cultures and the preset parameters suitable for the dissociation process. The thus supplied know-how may enable the easy establishment of initial values of the preset parameters.

The "reaction control unit" in the present invention is intended to control the dissociation of cells in the reaction vessel. The reaction control unit may include a chemical action control unit, a mechanical action control unit, and/or an environment control unit.

The chemical action control unit is intended to chemically/biochemically control dissociation reactions of cells in the reaction vessel. The chemical action control unit may be for example provided with: means of controlling the amount and concentration of chemical substances to be added to the reaction unit and also controlling the position and timing for addition of chemical substances (such as a processor and chemical preparing apparatus); means of adding the above-mentioned chemical substances (such as a liquid injecting apparatus); and means of increasing the amount of or discharging liquid in the reaction vessel (such as a liquid injecting apparatus and a liquid sucking apparatus). The chemical substances include a cell dissociating agent such as protease, dissociation neutralizer, pH adjustor, dye and the like. The chemical action control unit may be so constructed as to add a cell dissociating agent to the reaction vessel and start the dissociation treatment. It may also be so constructed as to add a dissociation neutralizer, cooled liquid or the like to the reaction vessel to which a cell dissociating agent has been added, thereby terminating the dissociating treatment. Moreover, it may be constructed such that the amount of the cell dissociating agent in the reaction vessel is increased if the dissociation treatment proceeds slowly.

The cell dissociating agent is not specifically restricted so long as it is capable of dissociating the connection between cells. It includes, for example, aprotease and/or chelating agent. Examples of a protease unrestrictedly include serine protease (such as trypsin, chymotrypsin, elastase, and plasmin), thiolprotease (such as papain, cathepsin B, cathepsin H, and cathepsin L), carboxyprotease (such as pepsin, cathepsin D, cathepsin E, and renin), and metalloprotease (such as collagenase and dispase). Examples of a chelating agent unrestrictedly include EDTA and EGTA. Any one or more than one of the foregoing may be used as the cell dissociating agent.

Examples of the dissociation neutralizer are not restricted and include, for example, any medium (such as a culture medium, physiological saline, and PBS which are suitable for cell life) which lowers the concentration of the cell dissociating agent, a substrate for protease contained in the cell dissociating agent, and metal to be chelated by the chelating agent contained in the cell dissociating agent.

The chemical action control unit may be constructed such that the amount of liquid in the reaction vessel is adjusted to prevent cells from planarly overlapping with one another. The amount of liquid in the reaction vessel may be appropriately measured by means of, for example, a level sensor or a weight sensor. With the amount of liquid reduced, there is little chance for cells to planarly overlap with one another. This helps calculate the particle size distribution by the image analysis method or laser diffraction scattering method.

The mechanical action control unit is intended to mechanically control the dissociation reaction of cells in the reaction vessel. The mechanical action control unit is provided with mechanical means by which to vibrate, rotate, and move up and down the reaction vessel, or to generate ultrasonic waves or water streams in the reaction vessel, thereby controlling the dissociation reaction. Examples of such mechanical means are not restricted and include a shaker, a stirrer of varied shape (rod, plate, propeller or the like) and material, a pump by which to generate water streams, and an ultrasonic generator. The mechanical actions are applied to the reaction vessel, thereby promoting the dissociation of the sheet-shaped cell culture. The mechanical actions to be applied may be invariable or variable according to a predetermined signal, for example based on a signal from the analysis unit.

The environment control unit is intended to control the dissociation reaction of cells by controlling the environment or an environmental condition in the reaction unit. The environment control unit controls the environment such as the temperature, humidity, carbon dioxide concentration, atmospheric pressure and the like in the reaction unit, unrestrictedly. To this end, the environment control unit may be unrestrictedly provided with a temperature control device (including a heater, a Peltier element, and a thermostat), a humidity control device (including a dehumidifier, a humidifier, a hygrometer, and a controller), a carbon dioxide control device (including a carbon dioxide generator, a ventilator, and a controller), and a pressure control device (including a decompressor, a compressor, and a controller). In a case where the cell dissociating agent is protease, the environment control unit may adjust and keep the atmosphere inside the reaction vessel at a temperature suitable for enzymatic activity, thereby initiating and advancing the dissociation reaction, or at a temperature unsuitable for enzymatic activity, thereby suppressing or stopping the dissociation reaction. The optimal temperature for protease varies depending on the kind of protease. Specifically, it is not restricted and is typically 35 to 40° C., 36 to 39° C., and 37 to 38° C. The temperature control inside the reaction vessel may be accomplished by directly heating or cooling the reaction vessel, for example through the temperature control device in contact with or adjacent to the reaction vessel, or by heating or cooling the periphery such as the air surrounding the reaction vessel.

The reaction control unit may be installed inside or outside the reaction unit, or may be installed partly inside and partly outside. For example, the reaction control unit may be attached to the support unit or may be so constructed as to support or enclose the reaction unit. Alternatively, the reaction control unit may be partly attached to the support unit and so constructed as to partly support or enclose the reaction unit. To be concrete, for example, the support unit and the temperature control device may be integrally formed so as to be hotplate-like, the support unit and mechanical action control unit may be integrally formed so as to be shaker-like, or the support unit and environment control unit may be integrally formed so as to be incubator-like. The shaker-like one integrally composed of the support unit and the mechanical action control unit may be placed inside the incubator-like environment control unit, or the incubator-like one integrally composed of the support unit and the environment control unit may be installed in the shaker-like mechanical action control unit.

As mentioned above, each component making up the system according to the present invention may be variously arranged as far as the desired objects can be achieved, and the components may be combined together or integrated if necessary.

Figure 1:
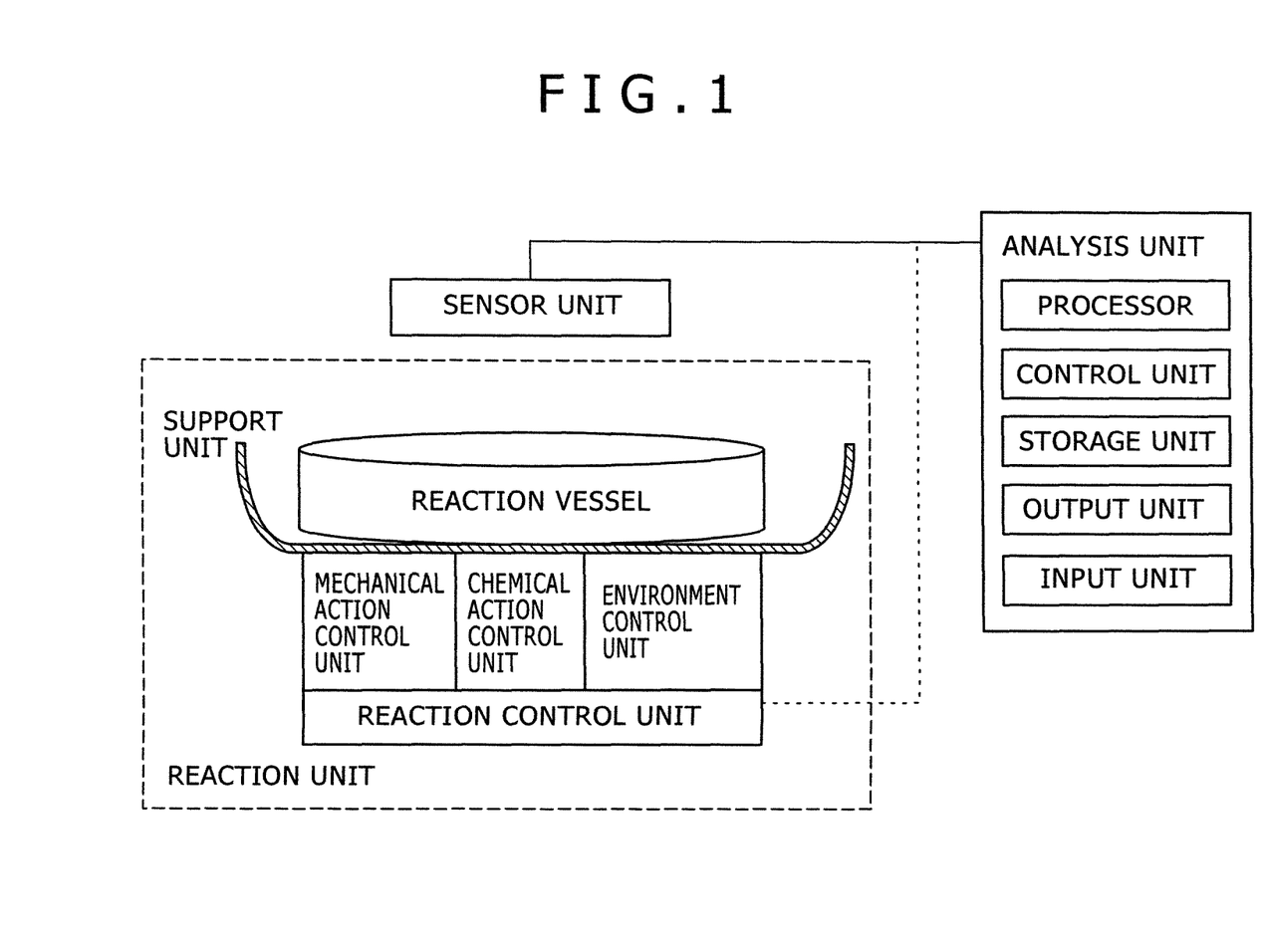
FIG. 1 is a block diagram of a system according to one embodiment of the present invention.

FIG. 1 is a block diagram of the system according to one embodiment of the present invention. In this embodiment, the system includes: the reaction unit including the reaction vessel and support unit; the reaction control unit including the mechanical action control unit, the chemical action control unit, and the environment control unit; the sensor unit; and the analysis unit including the processor, the control unit, the storage unit, and the input and output units. The reaction control unit is installed inside the reaction unit and integrated with the support unit. The sensor unit is placed above the reaction vessel. The analysis unit is installed outside the foregoing components and connected with them, so that the analysis unit transmits and receives preset parameters, measured parameters, and control signals. Needless to say, this block diagram merely shows one embodiment of the system according to the present invention, ant it should be understood that there are many possible ways, that differ from the block diagram, of arranging and combinating of the components.

Figure 2:
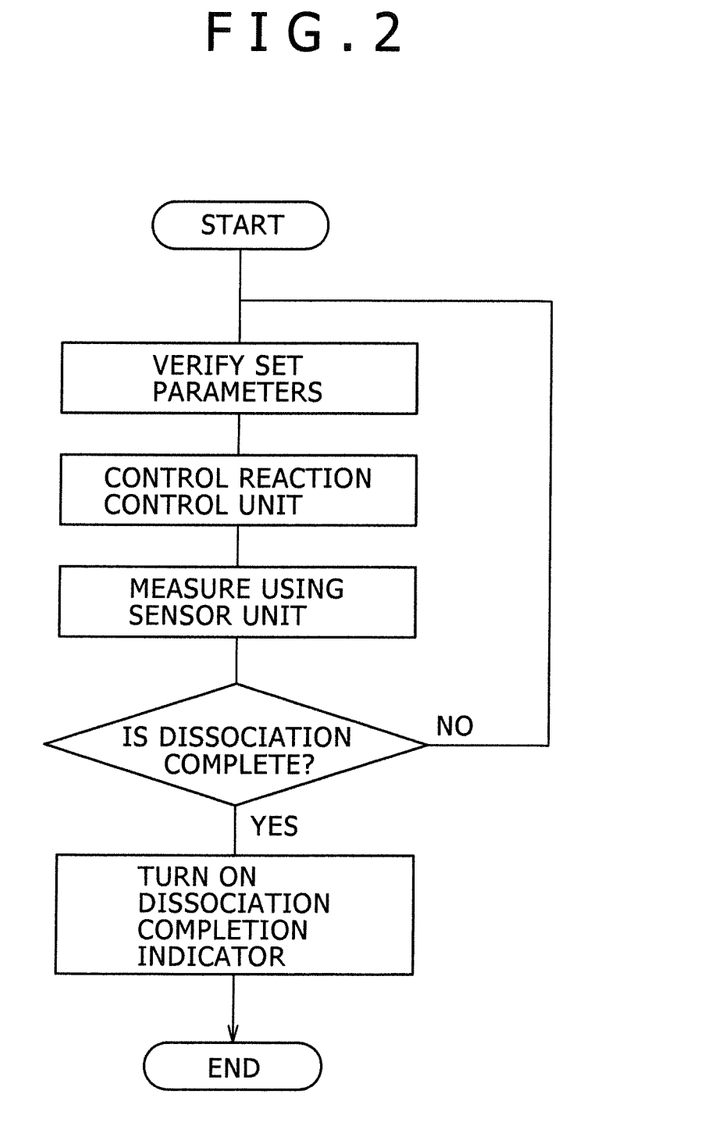
FIG. 2 is a flow diagram of a process for determining dissociation in the system according to one embodiment of the present invention.

FIG. 2 is a flow diagram showing the process for cell dissociation to be carried out in the system according to one embodiment of the present invention. In this embodiment, when the system receives an instruction to start the dissociation of a sheet-shaped cell culture, the system verifies the preset parameters and then sends the parameters (preset parameters) suitable for cell dissociation to the reaction control unit. The environment control unit in the reaction control unit measures the temperature inside the reaction unit and adjusts the temperature to the preset one. The chemical action control unit in the reaction control unit performs the chemical/biochemical treatment in the reaction unit, thereby advancing the dissociation of the connection between cells by the cell dissociating agent. The mechanical action control unit in the reaction control unit performs the mechanical operation (such as moderate vibration) on the reaction vessel, thereby advancing the dissociation. The reaction control unit carries out adjustment until the measured parameters inside the reaction unit reach the preset parameters, and then the sensor unit obtains information about the particle size distribution of cells existing in the reaction vessel.

Figure 3:
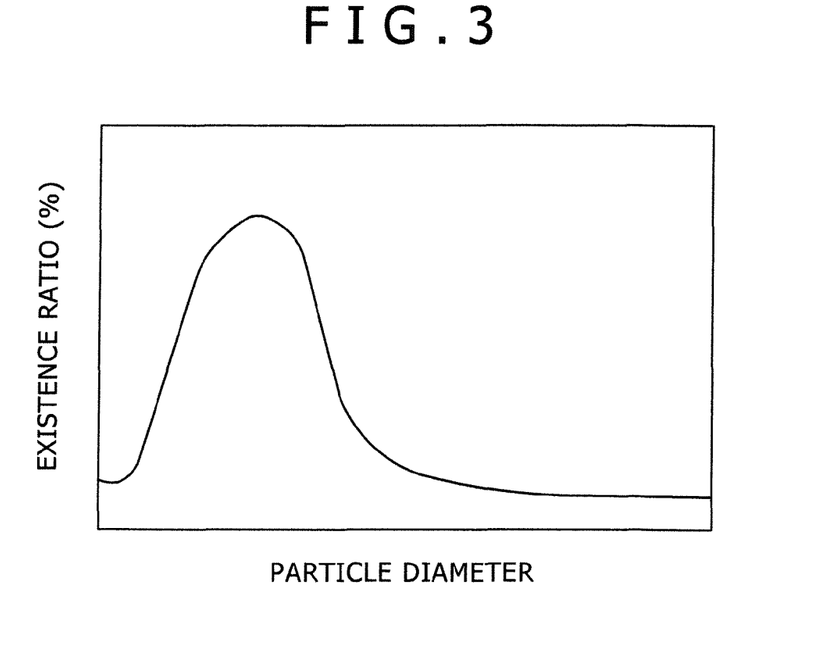
FIG. 3 is a diagram showing a particle size distribution of a sheet-shaped cell culture free of aggregates which was observed after the progress of dissociation.
Figure 4:
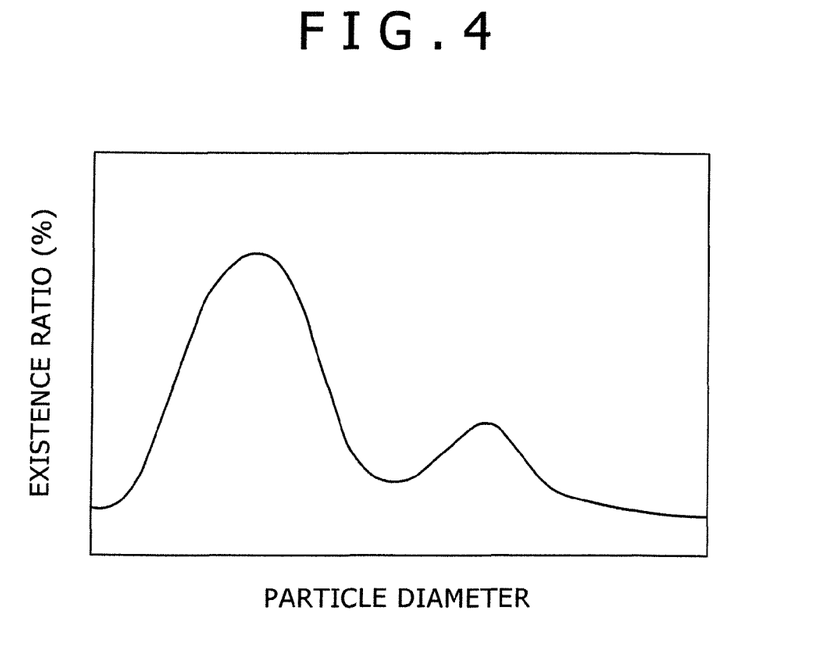
FIG. 4 is a diagram showing the particle size distribution of a sheet-shaped cell culture containing aggregates which was observed during the progress of dissociation.

The analysis unit calculates the particle size distribution of cells existing in the reaction unit from the information acquired by the sensor unit. Since the ratio of single cells having a small particle diameter becomes predominant as the dissociation proceeds, the particle size distribution will be an almost monomodal one having a peak equivalent to the average particle diameter of single cells, for example, as shown in FIG. 3. On the other hand, in a case where the cell culture remains undissociated (in the form of aggregates) during the dissociation treatment, the particle size distribution will have two peaks, one (left) due to single cells having a smaller particle diameter and one (right) due to cell aggregates having a larger diameter, for example, as shown in FIG. 4. This particle size distribution eventually becomes one having only a peak due to single cells having a small particle diameter as the dissociation proceeds and cell aggregates continue to be dissociated into single cells. The resulting particle size distribution remains unchanged with time. That is, when the particle size distribution becomes stable without changing with time, it indicates that the dissociation does not proceed any further and hence the dissociation is completed. Thus, in one embodiment of the present invention, knowing that the amount or rate of change in the particle size distribution becomes smaller than the preset parameters, the analysis unit can determine that the dissociation is completed. Upon completion of dissociation, the system outputs a dissociation completion signal, thereby terminating the process flow. Here, the reaction control unit may work independently from the analysis unit. For example, the reaction control unit may perform temperature control or vibration control during the analyzing process.

Needless to say, the flow diagram merely shows one mode of an action pattern of the system according to the present invention, and it should be understood that there are many other action patterns that could be deployed and that are different from the flow diagram.

The system according to the present invention may be connected and/or integrated with various apparatus, such as an incubator for cell cultivation, an apparatus for peeling off a sheet-shaped cell culture, and an apparatus for analyzing characteristics of dissociated cells. The last apparatus is exemplified by an apparatus for counting the number of cells (such as Coulter counter, made by Beckman Coulter, Inc.), an apparatus for automatically measuring the viability of cells, and a flow cytometer for measuring purity. The system configured in this way is capable of automatizing the steps from cell cultivation to preparation of a sheet-shaped cell culture and quantity control thereof.

The present invention relates also to a method of dissociating a sheet-shaped cell culture into individual cells, including the steps of:

(i) subjecting the sheet-shaped cell culture to a dissociation treatment;

(ii) acquiring information about a particle size distribution of cells in the sheet-shaped cell culture having undergone the dissociation treatment; and (iii) calculating the particle size distribution of cells from the acquired information, thereby determining and outputting a state of dissociation.

The dissociation in the present method includes an arbitrary step of dissociating cells constituting a sheet-shaped cell culture into individual single cells. Specifically, for example, cells may be dissociated by making the cell dissociating agent act in a medium suitable for the existence of cells, such as a culture medium, physiological saline, and PBS. The cell dissociating agent has been mentioned above in relation to the cell dissociation system. In a case where the cell dissociating agent is protease, the temperature of a reaction solution containing the sheet-shaped cell culture is adjusted to and maintained at a temperature suitable for the enzymatic reaction, whereby the dissociation is promoted. The optimal temperature for protease has been mentioned above. Incidentally, dissociation is promoted by moving the sheet-shaped cell culture in the medium after addition of the cell dissociating agent. This operation can be performed by, for example, vibrating the vessel, rotating the vessel, or moving the vessel up and down while the vessel contains the sheet-shaped cell culture or by generating ultrasonic waves or water streams in the vessel. The dissociation according to the present method may be carried out through at least the reaction unit and the reaction control unit of the cell dissociation system mentioned above.

The present method involves the steps of acquiring information about the particle size distribution of cells of the sheet-shaped cell culture having undergone a dissociation treatment, calculating the particle size distribution, and determining the state of dissociation. These steps are as mentioned above in relation to the cell dissociation system and may be carried out through at least the sensor unit and the analysis unit of the system. The present method may be implemented in one way according to the flow diagram shown in FIG. 2.

The present method may be self-contained, or may be incorporated as part of the flow or process from the preparation of a sheet-shaped cell culture to the quality control, the flow including the steps of cultivating cells constituting a sheet-shaped cell culture, preparing a sheet-shaped cell culture, peeling the sheet-shaped cell culture from the culture medium, dissociating cells from the sheet-shaped cell culture, and analyzing dissociated cells (for example for viability and purity).

The present invention relates also to a system intended to determine the state of dissociation of a sheet-shaped cell culture, the system including:

(i) a sensor unit which acquires information about a particle size distribution of cells in the sheet-shaped cell culture having undergone a dissociation treatment; and (ii) an analysis unit which calculates the particle size distribution of cells from the information acquired by the sensor unit, thereby determining and outputting the state of dissociation.

The present system has the sensor unit and the analysis unit, which are basically identical with those in the above-mentioned sheet-shaped cell culture dissociation system. The sensor unit in this system acquires information about the particle size distribution of cells (existing outside this system) in the sheet-shaped cell culture having undergone a dissociation treatment. The analysis unit calculates the particle size distribution on the basis of the thus acquired information and then determines the state of dissociation and outputs the result of determination. Therefore, this system may not include the reaction unit and/or the reaction control unit which are included in the sheet-shaped cell culture dissociation system. This system may be designed such that the sensor unit acquires information (such as image) about the particle size distribution of cells of the sheet-shaped cell culture undergoing a dissociation treatment for example in an incubator or a shaker separate from this system, and the state of dissociation can be determined and informed to the user or the like by way of voice, by lighting an indicator or the like.

The present invention relates also to a method for determining the state of dissociation of a sheet-shaped cell culture, the method including a step of determining the state of dissociation based on the particle size distribution of cells in the sheet-shaped cell culture having undergone a dissociation treatment. The step of determining the state of dissociation according to this method is carried out in the way described above in detail in relation to the cell dissociation system.

The cell dissociation system of the present invention will be described below in detail with reference to the accompanying drawings. The following description merely illustrates a specific example of the present invention and is not intended to restrict the scope of the present invention.

Figure 5:
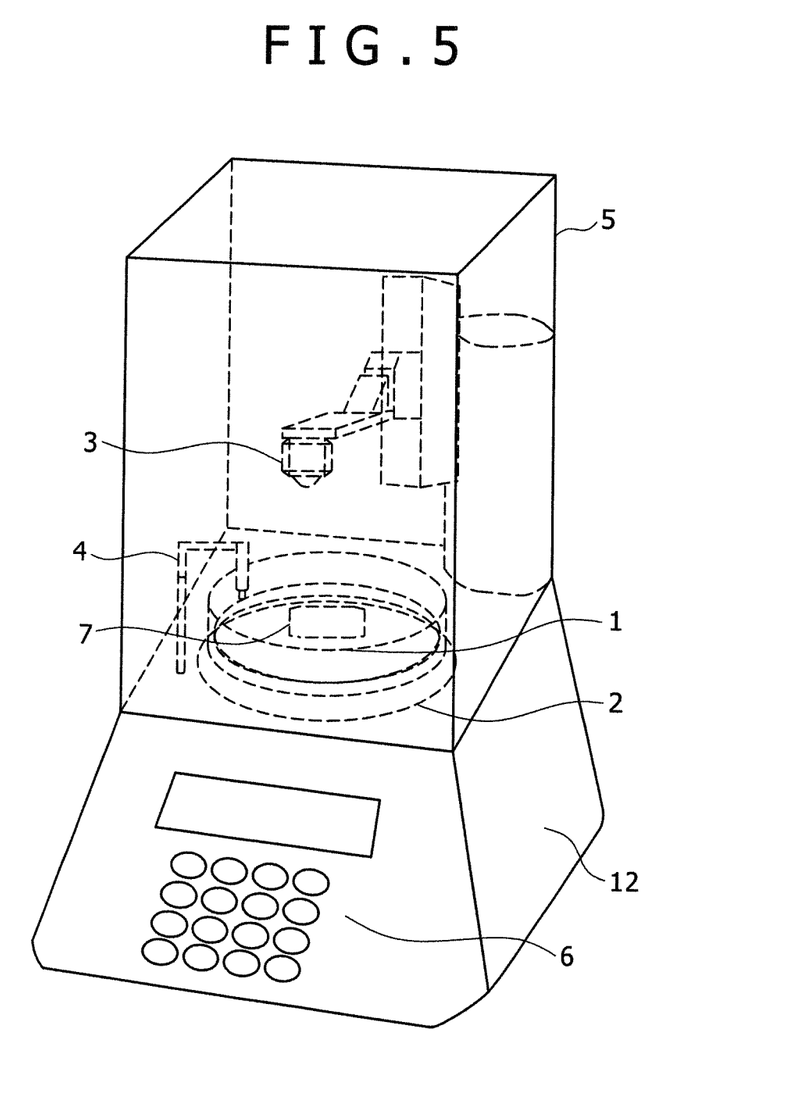
FIG. 5 is a diagram showing the whole of the system according to one embodiment of the present invention.
Figure 6:
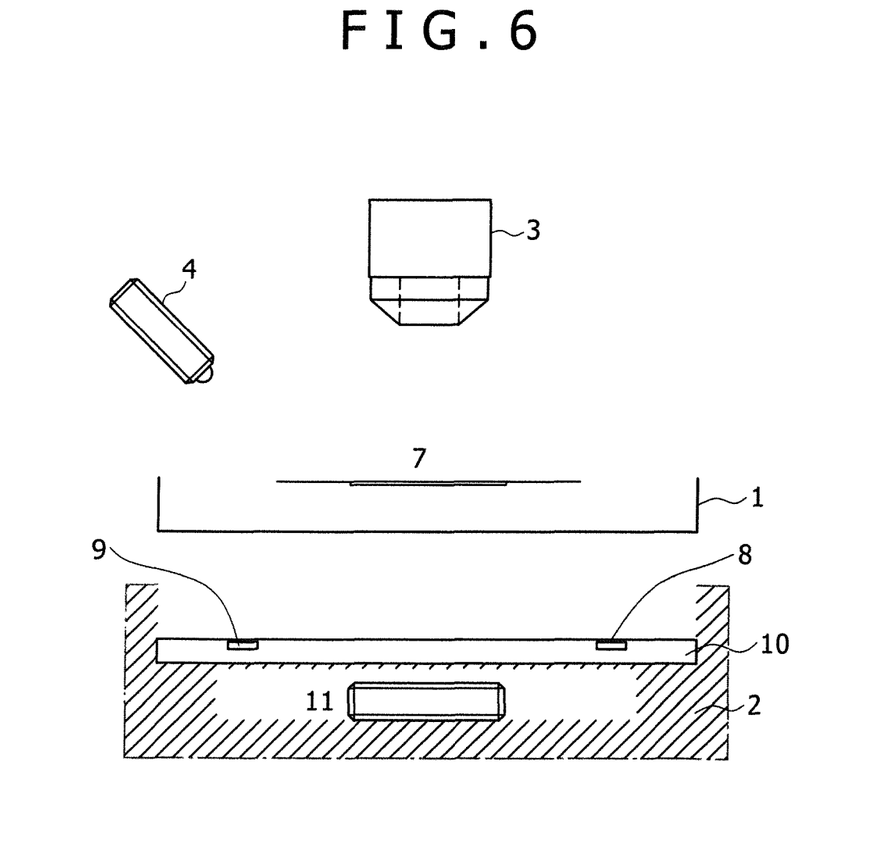
FIG. 6 is a sectional view showing part of the system according to one embodiment of the present invention.

FIGS. 5 and 6 are diagrams showing an embodiment of the cell dissociation system according to the present invention. FIG. 5 is a schematic diagram showing the whole of the system, and FIG. 6 is a sectional view showing an arrangement of components in a hood (5). According to the illustrated embodiment, a reaction vessel (1), which contains a sheet-shaped cell culture (7), is mounted on a vibratable support unit (2) provided with a temperature control function, which is enclosed in the hood (5). Above the reaction vessel (1) are arranged an injection nozzle (4) for injection of a cell dissociating agent or the like into the reaction vessel and a camera (3) for capturing an image of the inside of the reaction vessel. The support unit supports the reaction vessel above a temperature control plate (10) having a temperature measuring sensor (9) and a Peltier element (8). The support unit is provided with a light source (11) for illuminating the reaction vessel from below. Between the light source and the reaction vessel is placed a phase-contrast condenser or the like, that enables a contrast image from inside the reaction vessel to be obtained. The support unit is connected with a vibrating apparatus so that it can be vibrated. A main body (12) holds therein the vibrating apparatus, a reagent reservoir, a power unit, and a processor by which to evaluate the state of dissociation from the particle size distribution and to control various components. On the front of the main body is mounted an input/output interface (6).

Figure 7:
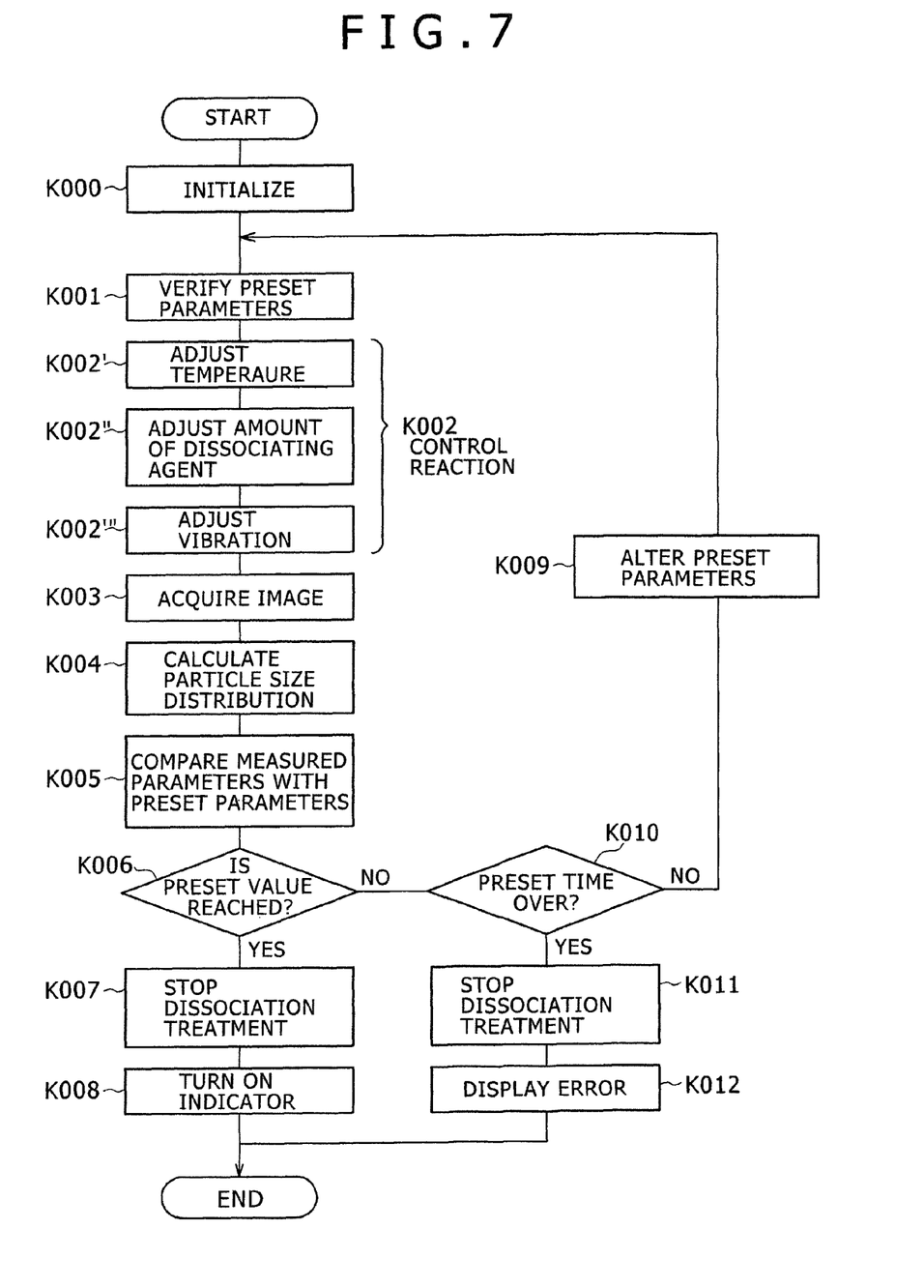
FIG. 7 is a flow diagram of a process for determining dissociation in the system according to one embodiment of the present invention.

A flow of the cell dissociation treatment in the above-mentioned system will be explained below with reference to a flow diagram shown in FIG. 7. After the reaction vessel containing a sheet-shaped cell culture is placed on the support unit, upon receipt of an instruction to start cell dissociation from the input/output interface (6), the system performs initialization (K000). That is, the system checks a normal action of each component and initial parameters (such as the temperature of the reaction vessel and the amount and level of liquid in the reaction vessel), thereby confirming an initial state of the system. Then, the system confirms preset parameters based on the initial state (K001). For example, the system can establish a timing for adjustment of an optimal temperature by knowing the fact that the temperature in the reaction unit is close to room temperature when the system is put to operation for the first time, but it is close to a previously established temperature in a case where the system has been used intermittently. The preset parameters may be established based on parameters entered from the input unit or previously stored parameters.

Figure 8:
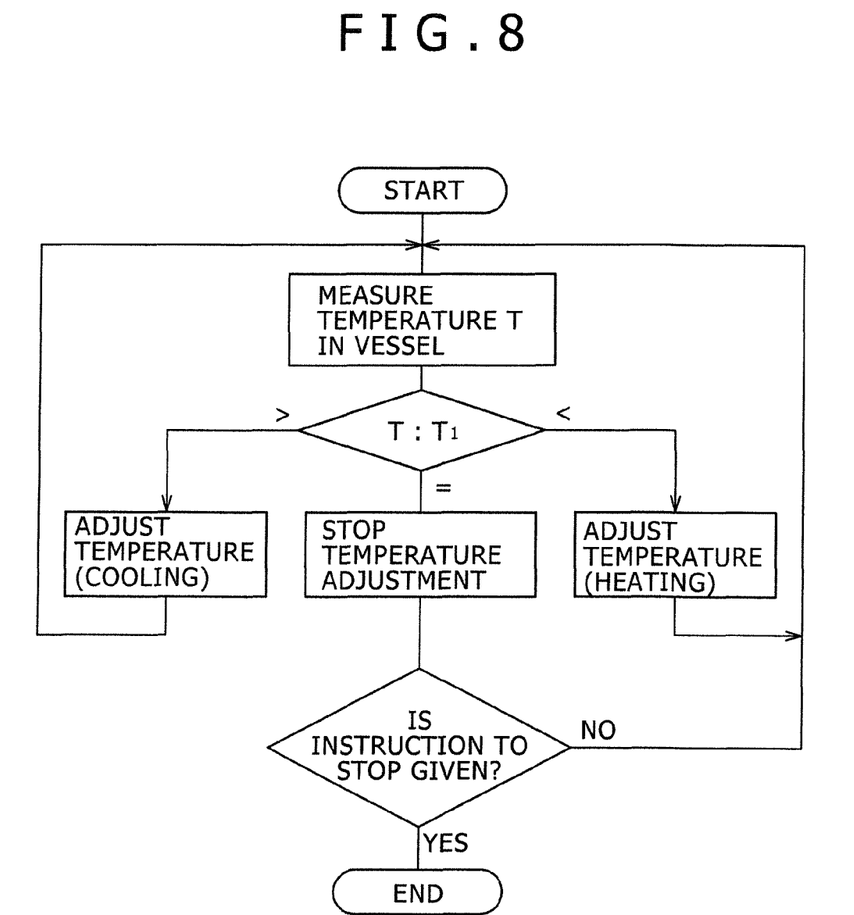
FIG. 8 is a flow diagram showing a subroutine process for temperature control in the system according to one embodiment of the present invention.

With the preset parameters confirmed, the system controls the dissociation reaction of cells in the reaction vessel (K002). The adjustment of temperature is performed by the temperature control plate so that the temperature in the reaction vessel is kept, for example, at 37° C. for adequate enzymatic reaction (K002'). The adjustment of the amount of the dissociating agent is performed so that the dissociation of the bonds between cells is promoted by the enzymatic reaction (K002"), This adjustment is accomplished by adjusting the concentration of the dissociating agent in the reaction vessel. The adjustment of vibration is achieved by adjusting the frequency and amplitude of the vibrating apparatus so that the rate of dissociation is controlled (K002'''). These adjustments may be carried out sequentially, simultaneously, or separately. The control of the reaction may be performed independently from the process flow of cell dissociation, as a combination of various sub-routines including subroutines for temperature adjustment as shown in FIG. 8. In other words, the reaction vessel in which cell dissociation is completed may be replaced by a next vessel, with the support unit kept at a constant temperature. In addition, the preset parameters may include detailed values including information about time. For example, with such detailed preset parameters, it may be possible to stop vibration only when the sensor unit acquires information or to alter a mode of vibration at prescribed intervals.

After the reaction control has been carried out adequately, the system acquires an image of cells existing in the reaction vessel (K003). At this time, the system may adjust the light source and focus the camera so as to create optimal imaging conditions. In addition, the system may add a dye for staining cells into the reaction vessel through the injection nozzle, thereby staining cells in the reaction vessel, if it is difficult to detect the contour of cells or if it is necessary to determine viability of cells at the same time. After that, the system estimates the size, volume, and number of cells from the thus acquired image and then calculates the particle size distribution (K004). Next, the system compares the measured parameters (including the particle size distribution and information about the environment in the reaction vessel) with the preset parameters, thereby analyzing the state of dissociation and the state inside the reaction unit (K005), and determines whether or not the state of dissociation (such as the average particle diameter, the amount and rate of change of the average particle diameter with time, and the particle size distribution pattern) has reached the preset value (K006).

If the state of dissociation has reached the preset value, the system adds a dissociation neutralizer from the injection nozzle into the reaction vessel and/or lowers the temperature of the temperature control plate, thereby stopping the dissociation treatment (K007). The system also informs the user of the completion of the dissociation treatment by turning on the indicator (K008).

On the other hand, if it is determined that the state of dissociation has not yet reached the preset value, the system determines whether or not the duration of dissociation has exceeded the preset value (K010). In a case of negative determination, the system alters the preset parameters according to need (K009) and repeats step K001 and subsequent steps. In a case of positive determination, the system stops the dissociation treatment in the same way as in step K007 (K011) and informs the user of an error (K012).

The series of steps in the foregoing flow may be carried out simultaneously or in a different order or may be partly omitted. For example, the step of adjusting temperature (K002') may be followed by the step of comparing the measured parameters with the preset parameters (K005) and further by the step of adjusting the amount of the dissociating agent (K002") and the step of adjusting vibration (K002'''). That is, in a case where the dissociation treatment in the reaction vessel is previously carried out outside the reaction unit and then placed into the system for determining the state of dissociation, the system will determine, by comparison between the measured parameters and the preset parameters (K005), such that there is no need for the control of reaction. In this case, it is possible to omit the subsequent step of adjusting the amount of the dissociating agent (K002") and the step of adjusting vibration (K002'''). The step of stopping dissociation (K007 or K011), and the step of turning on the indicator (K008) or displaying an error (K012) may be carried out simultaneously. Alternatively, the former step may be carried out after the latter step. Further, in a case where it is determined that the state of dissociation has not yet reached the preset value (K006) in the process flow mentioned above, the system may calculate optimal parameters from the result of the comparison between the measured parameters and the preset parameters (K005) and alter the preset parameters (K009).

The cell dissociation system according to the present invention has been described above. It may be variously embodied in other ways than mentioned above. Therefore, various embodiments modified from the foregoing embodiments without departing from the gist of the present invention are also included in the scope of the present invention, and such modifications may be easily understood by persons skilled in the art.

The invention claimed is:

1. An automated system for dissociating an already formed sheet-shaped cell culture into individual cells and with the sheet-shaped cell culture being formed by a selected type or types of cells, the automated system comprising:
   a reaction unit having a reaction vessel including an interior thereof that is configured to receive a cell dissociating agent and the already formed sheet-shaped cell culture so that the already formed sheet-shaped cell culture undergoes a cell dissociation reaction via the cell dissociating agent in the reaction vessel for the purpose of determining the competence of the sheet-shaped cell culture for transplantation;
   a sensor unit configured to acquire information relating to particle size existing in the interior of the reaction vessel which includes single cells and cell aggregates from the dissociating sheet-shaped cell culture as the sheet-shaped cell culture undergoes the cell-dissociation reaction, the sensor unit being disposed adjacent to or in the reaction vessel to permit the sensor unit to acquire the particle size information from particles in the reaction vessel interior as the cell-dissociation reaction is occurring;
   an analysis unit including a processor that is configured to receive the particle size information from the sensor unit, calculate a particle size distribution in the reaction vessel based on the particle size information received from the sensor unit, monitor change of the particle size distribution from a first particle size distribution state having multiple peaks of particle size concentration with one of the peaks resulting from single cells having a smaller particle size and another of the peaks resulting from cell aggregates having a larger particle size toward a second particle size distribution state having a single peak of particle size concentration resulting from single cells having the smaller particle size, and determine a state of dissociation of the already formed sheet-shaped cell culture in the reaction vessel based on the monitored change of the particle size distribution from the first particle size distribution state toward the second particle size distribution state, the analysis unit further including a signal generation circuit that generates and outputs a signal indicating the state of dissociation as determined by the processor; and
   a reaction control unit configured to receive the outputted signal indicating the state of dissociation and being operatively connected to the reaction vessel for controlling the cell dissociation reaction therein, the reaction control unit being configured to, based on the received the outputted signal indicating the state of dissociation, cause the cell dissociation reaction in the reaction vessel to stop when the second particle size distribution state exists for avoiding damage to the dissociated single cells from the already formed sheet-shaped cell culture,
   wherein the processor of the analysis unit is further configured to determine at least one of a plurality of parameters related to progress of the dissociation reaction toward completion based on the particle size information received from the sensor unit and to compare the at least one parameter to a corresponding preset parameter that indicates completion of the dissociation reaction, the plurality of parameters including average particle size in the reaction vessel, chronological amount of change or chronological rate of change of the average particle size in the reaction vessel, and a pattern of the particle size distribution, the analysis unit being further configured to determine and output the state of dissociation to the reaction control unit based on the comparison between the at least one parameter to the corresponding preset parameter for controlling either the continuation or the termination of the cell dissociation reaction in the reaction vessel.

2. The automated system of claim 1 wherein the reaction vessel is sized to receive the already formed sheet-shaped cell culture to avoid overlap of cells of the already formed sheet-shaped cell culture in the reaction vessel.

3. The automated system of claim 1 wherein the reaction control unit includes a supply device including a nozzle for supplying the dissociating agent and a dissociation neutralizer into the reaction vessel with the reaction control unit controlling operation of the supply device to regulate supply of the dissociating agent into the reaction vessel if the outputted signal indicating the state of dissociation received by the reaction control unit is based on the first particle size distribution state and to initiate supply of the dissociation neutralizer into the reaction vessel if the outputted signal indicating the state of dissociation received by the reaction control unit is based on the second particle size distribution state.

4. A method of dissociating a sheet-shaped cell culture into individual cells using the automated system of claim 1, the method comprising:
   (i) a step of subjecting the sheet-shaped cell culture to a dissociation treatment;
   (ii) a step of acquiring information about a particle size distribution of cells in the sheet-shaped cell culture having undergone the dissociation treatment; and
   (iii) a step of calculating the particle size distribution of cells from the acquired information, thereby determining and outputting a state of dissociation.

5. The method as defined in claim 4, wherein the sheet-shaped cell culture contains a skeletal myoblast.

6. The method of claim 5, including the steps of cultivating cells constituting the sheet-shaped cell culture, peeling off the sheet-shaped cell culture, and transferring the sheet-shaped cell culture to the reaction vessel.

* * * * *